March 27, 1934. E. E. HARRINGTON Re. 19,119

CATAMENIAL APPLIANCE

Original Filed June 15, 1928

Inventor

Earl E. Harrington

By

Charles B. Mann Jr.

Attorney

Reissued Mar. 27, 1934 Re. 19,119

UNITED STATES PATENT OFFICE 19,119

CATAMENIAL APPLIANCE

Earl E. Harrington, Washington, D. C., assignor to Max Hain, Los Angeles, Calif.

Original No. 1,730,818, dated October 8, 1929, Serial No. 285,547, June 15, 1928. Application for reissue June 20, 1931, Serial No. 545,796

9 Claims. (Cl. 128—289)

The invention is illustrated in the accompanying drawing, wherein,—

Figure 1:
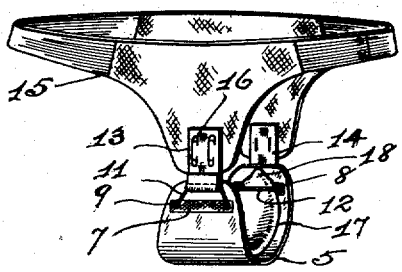
Fig. 1 shows the improved device attached to and suspended from a body band with a pad in place thereon, the parts being shown in perspective.
Figure 2:
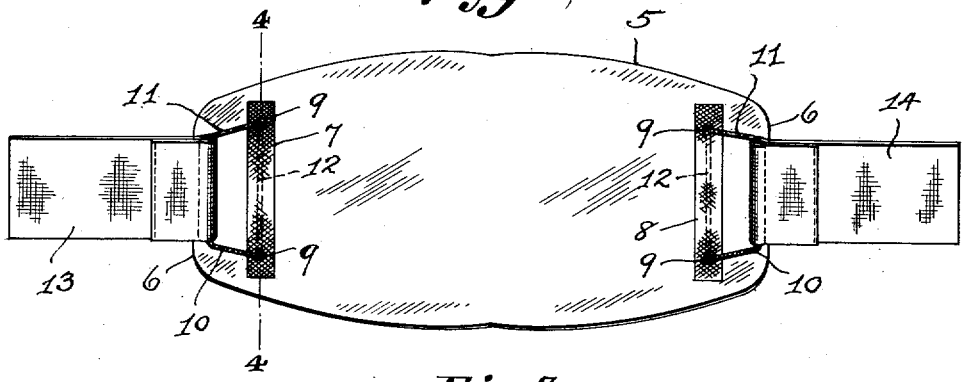
Fig. 2 illustrates the pad-carrier and its attaching tabs as viewed from the under side.

Referring to the drawing, the numeral 5 designates a pad-carrier and protector of a general rectangular shape and preferably formed of a sheet of thin rubber or moisture-proof material.

Near each end, but spaced from the end edges 6 thereof, the pad-carrier and protector has cross-wise reinforcements 7 and 8 therein which comprise fabric strips embedded or cured in the rubber sheet.

Perforations 9 are provided in the pad-carrier in spaced relation, and these perforations extend through the rubber sheet as well as through the fabric strips or reinforcements 7 and 8.

The perforations 9 are arranged in pairs in that one of them passes through the pad-carrier and strip near one side of the carrier while the other passes through the pad-carrier and strip adjacent to the opposite side of the carrier.

An elastic or flexible cord 10 is fed through the perforations from one side of the carrier to the opposite side thereof whereby to form two loops 11 and 12,—the loop 11 being on the under side of the carrier while the loop 12 is at the upper side of said carrier and is to be utilized as a clamp as and for a purpose that will presently be more fully explained.

One loop 11 at one end of the carrier has a fabric tab 13 attached thereto while the loop 11 at the opposite end of the carrier has a fabric tab 14 attached to it.

The two tabs 13 and 14 are provided for attachment to a belt structure 15, which encircles the body of the wearer but which latter forms no part of my invention.

The means employed to attach the tabs 13 and 14 to the belt structure may vary, but in the present instance, I show safety-pins 16 for this purpose.

Figure 3:
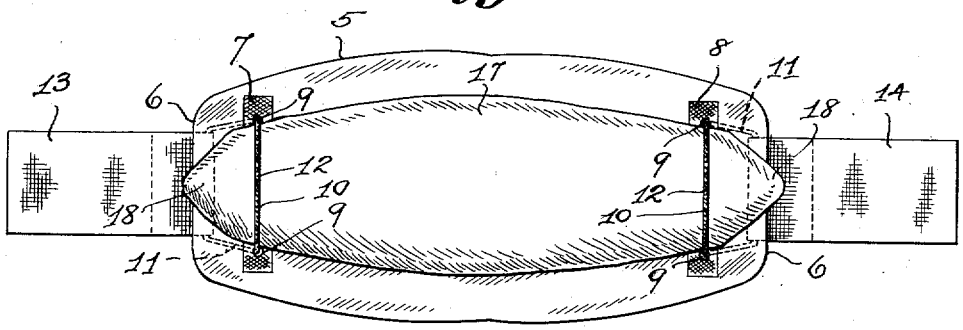
Fig. 3 shows the pad-carrier, tabs, pad-clamps and pad as viewed from the upper side thereof.
Figure 4:
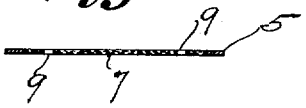
Fig. 4 illustrates a cross-section through the pad-carrier as viewed on the line 4—4 of Fig. 2.

In practice, the sanitary pad 17 of any preferred form is laid upon the upper side of the pad-carrier and protector, as shown in Figs. 1 and 3 of the drawing, and the two ends 18 of the pad are slipped beneath the loops 12.

When the appliance is attached to the belt-structure 15, the tabs 13 and 14 which engage the under loops 11, draw on the cords 10 and pull the loops 12 taut at the upper side of the carrier and clamp the ends 18 of the sanitary pad in place against the pad-carrier and protector and hold the same from displacement.

The strain therefore on the tabs causes the clamping loops 12 to engage and hold the pad while the reinforcements 7 and 8 prevent the cords from tearing the rubber of the carrier and thus maintain the upper and lower loops in the cord.

Having described my invention, I claim:—

1. A catamenial appliance comprising a flexible pad-carried and protector having a looped cord passing therethrough at each end thereof, the loop of the cord extending crosswise over the pad-supporting face of the carrier and serving to clamp the ends of a pad and means for supporting the carrier by the looped cords whereby to draw the loops in clamping engagement with the ends of the pad laid upon the carrier.

2. A catamenial appliance comprising a pad carrier and protector comprising a sheet of moisture-proof material having reinforcements near each end thereof with a pair of spaced perforations extending through said sheet and reinforcements, a cord passing through said spaced perforations and extending crosswise over the pad-supporting surface of the carrier whereby said crosswise portion of the cord will form a clamp at one side of the carrier, and a tab attached to each cord at the opposite side of said carrier whereby when a pull on the tabs takes place on the one side of the carrier the crosswise portions of the cords will be drawn toward the opposite side of the carrier to clamp a pad thereagainst.

3. A pad carrier and protector comprising a flexible pad carrying member, a pad adapted to be disposed thereon, means for supporting said pad carrying member comprising a looped cord mounted loosely on the pad carrying member and adapted to embrace the pad when arranged thereon to bind said pad to said carrier, said cord forming supporting means for the pad carrier and adapted to secure the pad on the pad carrier when strain is placed on the same when in position on a user.

4. A device of the kind described comprising a flexible pad carrier, a cord loosely carried by the carrier for embracing the pad when arranged upon said carrier, said cord being movably mounted in respect to said carrier, a support, a connection between said support and said cord, said cord being placed under tension when strain is placed upon said support when in position upon a user to bind a pad upon the carrier.

5. A pad carrier comprising a holder formed of a strip of flexible material adapted to support a pad, a looped cord movably mounted on the holder and adapted to embrace and hold said pad on said strip of flexible material and forming supporting means for the carrier and pad, said cord being placed under strain and binding the pad on the holder when in position upon a user.

6. A device of the kind described comprising a flexible pad carrier upon which a pad is adapted to be arranged, a looped cord loosely carried by the carrier and adapted to embrace said pad to hold said pad on said carrier, said cord forming means for supporting the carrier and being adapted to bind the pad on the carrier when strain is placed on the same when in position on a user.

7. A device of the kind described comprising a flexible pad carrier for supporting a flexible pad, a cord loosely carried by each end of the carrier adapted to engage each end of the pad and bind it thereon and supporting means for the carrier having a connection with the adjacent cord to draw the cords into engagement with the pad upon the carrier and bind the pad thereon when strain is placed upon the supporting means when in position on a user.

8. A bandage holder of the kind described comprising a carrier formed of a flexible strip upon which a flexible pad is adapted to be placed and having means disposed at its ends for supporting the same, a loop loosely mounted on each end of the carrier and having a connection with said supporting means for binding the pad and supporting the carrier, said loop being adapted to embrace the pad thereon and to bind said pad upon the carrier when strain is placed upon the supporting means when in position upon a user.

9. A carrier of the kind described comprising an oblong shaped flexible member for supporting a pad and upon which a pad is adapted to be disposed, means at one end for supporting a carrier, a movable cross member arranged over the pad on the carrier and forming a part of the supporting means, said cross member being adapted to bind the pad on the carrier and support the carrier when strain is placed upon the supporting means when in position upon a wearer.

EARL E. HARRINGTON.